United States Patent
Webb et al.

(10) Patent No.: US 6,325,756 B1
(45) Date of Patent: Dec. 4, 2001

(54) CONCEPTS TO IMPLEMENT MEDCONNECT

(75) Inventors: James D. Webb; Chester G. Nelson, both of Maple Grove; James G. Thies, Champlin; Ronald A. Stauffer, Coon Rapids, all of MN (US)

(73) Assignee: Medtronic, Inc., Minnneapolis, MN (US)

( * ) Notice: Subject to any disclaimer, the term of this patent is extended or adjusted under 35 U.S.C. 154(b) by 0 days.

(21) Appl. No.: 09/381,263

(22) PCT Filed: Mar. 27, 1998

(86) PCT No.: PCT/US98/06085

§ 371 Date: Sep. 17, 1999

§ 102(e) Date: Sep. 17, 1999

(87) PCT Pub. No.: WO98/42407

PCT Pub. Date: Oct. 1, 1998

Related U.S. Application Data

(60) Provisional application No. 60/042,367, filed on Mar. 27, 1997.

(51) Int. Cl.[7] .............................. A61B 5/00; A61N 1/08
(52) U.S. Cl. ............................ 600/300; 607/32; 607/60; 600/522; 128/904
(58) Field of Search .................................... 600/300–301, 600/522–523; 607/30–32, 60; 700/2–3, 83; 345/5, 343–345; 709/232–238, 201–202; 128/902–905, 920–925; 379/106.02

(56) References Cited

U.S. PATENT DOCUMENTS

| | | | |
|---|---|---|---|
| 4,098,267 | 7/1978 | Stein | 128/2.06 G |
| 4,317,956 | 3/1982 | Torok | 178/18 |
| 4,377,852 | 3/1983 | Thompson | 364/900 |
| 5,168,269 * | 12/1992 | Harlan | 340/709 |
| 5,235,680 | 8/1993 | Bijnagte | 395/161 |
| 5,241,625 | 8/1993 | Ephard | 395/163 |
| 5,263,869 | 11/1993 | Ziv-El | 434/336 |
| 5,309,919 * | 5/1994 | Snell et al. | 607/32 |
| 5,384,643 | 1/1995 | Inga | 358/403 |
| 5,431,691 | 7/1995 | Snell | 607/27 |
| 5,452,299 | 9/1995 | Thessin | 370/62 |
| 5,487,754 | 1/1996 | Snell | 607/27 |
| 5,487,755 | 1/1996 | Snell | 607/27 |
| 5,752,977 | 5/1998 | Grevious | 607/32 |

\* cited by examiner

*Primary Examiner*—Robert L. Nasser
*Assistant Examiner*—Michael Astorino
(74) *Attorney, Agent, or Firm*—Girma Wolde-Michael; Reed A. Duthler

(57) ABSTRACT

A medical device implant, monitoring and adjustment are enhanced by the telepresence of a remote expert (31) having a screen display (30) that mirrors the display at the patient location. Pointers (51), whether they can activate subprograms at the patient location or not, are moved identically at both locations at the same time. Also, the ECG and any features thereof are updated in real time, while other communication operations occur.

8 Claims, 12 Drawing Sheets

– REMOTE RESPONSE –

CONCEPTS TO IMPLEMENT MEDCONNECT

This appln is a 371 of PCT/US98/06085 filed Mar. 27, 1998 which claims benefit of Prov. No. 60/042,367 filed Mar. 27, 1997.

This invention relates to communication and coordination facilities which enable a remote expert to easily facilitate understanding of communication to a local actor in real time. Particularly, this invention relates to application of such systems to active surgery situations and clinical environments in which the visual display screens of the remote and distant locations must be tightly coordinated, and is especially applicable to such situations where a pointer and a time varying physiological signal may be displayed on the same screens at the same time.

BACKGROUND

During surgery or for follow-up to determine the present functionality or to change functionality for implanted medical devices, it can be important for an expert at a remote site to know how the implant is responding and what the local actor dealing with the implant and/or the patient is doing in real time. There is very little acceptance for confusion in such circumstances and having a real time system display available to both the remote actor and the local actor will go a long way to eliminating the potential for confusion.

Similar communications and remote functioning have been attempted previously. It is believed that none of the prior systems are particularly well suited to the surgical or clinical environments, and particularly not to those where implanted medical devices are being used. By enabling remote pointing and physiologic display coordination, rapid and exact communications about the condition of the device and/or the patient and any peculiarities in the display can be noted and controlled for across large distances. Thus a single expert could be "virtually" at many distant locations in a single day using such a system without leaving the situs of his computer. A list of references where similar inventions in the same or other fields were contemplated follows, and these are incorporated herein by this reference thereto.

Epard et al, U.S. Pat. No. 5,241,625,

Inga et al., U.S. Pat. No. 5,384,643,

Thompson U.S. Pat. No. 4,377,852,

Ziv-El U.S. Pat. No. 5,263,869,

Thessin et al. U.S. Pat. No. 5,452,299,

Harlan U.S. Pat. No. 5,168,269,

Torok, et al. U.S. Pat. No. 4,317,956,

Stein et al. U.S. Pat. No. 4,098,267, and

Bijnagte U.S. Pat. No. 5,235,680.

There have been remote device operations used before, wherein a remote expert could control what was occurring on a local technicians station, including for example, the model 89441a Vector Signal Analyzer™ from Hewlett Packard, but no prior devices of which the inventors are aware include the features of this disclosure which are particularly suited to remote expert supervision of a local implantable medical device operation. The instant disclosure relates particularly to allowing for repeatable remote near real time ECG, EGM, and marker channel information at the same time display and allowing for dual site manipulation of a pointer on the display at both locations without having conflict. [In this document we will use various terms such as ECG, EGM, EKG and Marker Channel information to represent that such types of information as the intracardiac electrogram or surface ECG's, with or without additional marker channel information are all signals that could be found in the display window for whatever physiologic signal that the local attendant and remote expert may desire to look at simultaneously. Accordingly, any such use of these terms should be assumed to apply to the use of any of these terms for any similar physiologic signals, with or without device information superimposed thereon, such as Marker Channel information.]

The primary use of the invention is believed to be pacemaker/defibrillator follow-up and implant where an expert is remote from the patient's local situs where such operations are occurring. What is believed to be needed is a communications system for communicating in real time or near real time the position of a pointer that is manipulable at more than one location on simultaneous displays at two locations so that the pointer will appear at the same location in the remote display as the local display regardless of any conflicting instructions given by users at the remote and local locations. Provision is made to allow for simultaneous activation of two pointers, one controlled by the expert and one by the attending technician/physician. Each has a unique icon in our preferred system embodiment.

This system should have simultaneous displays for communicating and where necessary, enhancing the ECG signal available for remote display such that it appears to move like a normal ECG at the remote location with minimal difficulty and movement occurs n near real time. Of particular concern in using typical remote viewing systems is that screen displays occasionally have lossy displays, so a short term change in a physiologic signal may be missed at the remote location. The sweep-bar or smooth movement of the signal should ideally be maintained. The availability of such a system would help a great deal in surgery and particularly cardiac surgery. It could also find application to the cardiac pacemaker clinic follow up. With a coordinated cursor or pointer only one of the remote and local actors can adjust its position at a given moment, and there can be no confusion as to what location in the display they are both communicating about through some other telephonic aural or video link which should be operative simultaneously to best employ the inventive features described herein.

What such a system would enable is the review by an expert on either the patient (as in a doctor, for example) without this expert needing to be present in real space. It alternatively and simultaneously could be used for the consultation of a local physician or surgeon with a systems expert that may have intimate knowledge about the components of the devices that are generating the EKG signal and performing other functions in the surgical or clinical locality.

SUMMARY OF THE INVENTION

Figure 3:
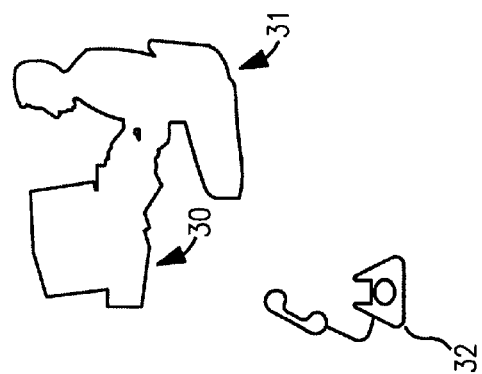
FIG. 3 is an illustration of a distant expert and his computing device.

Various aspects related to remote communications are herein described with particularly here and claimed, those improvements provide a new system image the features of a moving remote ECG or other physiologic signal display and real time remote pointer coordination.

In general a personal computer with a microprocessor and memory that contain appropriate software to configure them to operate as detailed herein is connected to a programmer which has similar and interrelated components, via any one of a number of methods including modem connections over telephone lines, DSVD modems, wireless, or internet, or any other similar form of communications link that may be in use and easily available. In other words, the system would employ a set of at least two devices having a display at a remote and at an operating location and communications pathways between, that communicate a coordinated display of information on the remote location display and in the operating location display such that communications are enhanced between the users at the two locations by use of the two coordinated display means at the remote and local operating (i.e. programmer) locations. The local display may also display local information to the local user that is uncoordinated with or completely separate from information displayed at the distant site display if desired. For examples, a battery power available display may appear on a local portable device display, that is unnecessary for the distant location to be aware of; or an expert system window could be available to the local display of the remote expert actor which is unavailable to the display at the location of the operating room surgeon.

At one end is the programmer device for use in medical communications systems for communicating in near real time information from between at least two remote sites, one remote site at a patient location having the programmer device which has a programmer generated display, and an other of said at least two remote sites at an expert location having a computing device with a computing device generated display, each location having available substantially similar screen displays, such that information related to an implantable medical device and a patient at said patient location remote site can be reviewed simultaneously on said substantially similar displays at said at least two remote sites facilitated by data communications transferred across a communication line between said at least two remote sites, said programmer device being configurable to perform various operations by executing programs through a microprocessor and memory system although many of the programs could be converted to hardware having limited functionality. This programmer then would have a physiologic signal device connection, connected to said programmer device for receiving electrical output representing a patient's physiologic signal waveform, and for producing a signal suitable for use by a programmer screen display operating program for generating a display from said electrical output at at least one display area including at least a physiologic waveform signal display area and producing instantaneous changes in said at least one display area, at least one of said changes representative of changes in said waveform. The programmer display operating program, would use a number of elements including at least a first video display data buffer for holding a video data representation of information displayed in one of said at least one display areas of said programmer generated display, a second video display buffer for holding data representing instantaneous changes in at least one of said areas, a display generating program for using a data image of said video data representation in said first video display buffer for producing said programmer generated display, and it would also have an index generating program for reviewing data in said first video display buffer and creating a first index buffer corresponding to said at least one of said display areas, said index generating program indicating in said first index buffer by storing data therein representing which of all locations in said at least one area have changed from a previous review, and for capturing a data representation of said changed locations in a capture buffer and, a sending program for packaging data comprising contents of said first index buffer and said capture buffer in appropriately encoded format, and for sending said appropriately formatted index buffer data across the communication line so as to get the information to the other remote site(s).

Preferably, the display generating program also has a two color display generating program for interpreting said physiologic signal waveform as two color display data, and wherein said index generating program has a data compression program for receiving said physiologic waveform index data and coding it such that for each byte, one bit is set to indicate whether a change has occurred in that byte and such that for the entire physiologic waveform index buffer, a compressed physiologic waveform index is prepared.

The programmer operating program preferrably also has a pointer/cursor coordination program having a buffer for holding at least location information for each pointer/cursor to be coordinated, and having a monitoring means for updating any programmer generated display change in pointer/cursor activation and location, said monitoring means updating each said pointer/cursor buffer with any change in location information from a last review, said location information being changeable responsive to pointer/cursor user controls based on a local user changing location status of any pointer/cursor under local control, and wherein said pointer/cursor coordinating program further comprises a buffer for containing information regarding at least location status of each remote pointer that is to be displayed on said patient location display. The programer operating program having these pointer/cursor features operates with the patient location screen display operating program, which to work with these pointer/curosr features has a program for receiving new information for each said remote pointer/cursor buffer and operating on such data to produce a display of said remote pointer/cursor in accord with the data in said remote pointer/cursor buffer such that any changes in the location data of a remote pointer/cursor buffer results in a change in location on the display of that remote pointer/cursor on the patient location display screen.

Preferably, the pointer cursor operating program also has an activation buffer for maintaining activation status for each pointer/cursor capable of activation. But if activation is not available from a remote pointer/cursor, such a buffer would not be needed for the activation status of that particular icon, although it could be useful information and used at the programmer site to inform the programmer user that the expert has indicated that the expert thinks this particular pointer/cursor should activate a particular function, even if it is not activatible by the expert communicating from the remote site. In some embodiments the expert will be able to remotely activate features on the programmer though such a feature.

Of course, to activate the features of pointer/cursors we prefer to include in the programmer device a pointer data capture program for capturing and then for sending the data in said pointer/cursor buffer to said communication line.

Additionally, we prefer to include a program for monitoring which of all said pointer/cursors is active such that said active cursor/pointer may initiate a command, and for maintaining a data buffer containing such monitored information.

Preferably, the computing device operating program for coordinating a physiologic waveform display with a programmer generated display will have a communication means to receive data sent by said programmer device and to produce a physiologic waveform display therefrom.

On the other side of the system(s) we prefer a computing device operating program for displaying an image substantially the same as the display on the programmer generated display having communications means to receive data sent by the programmer and generating a substantially similar display therefrom.

This of course preferably comprises a system for displaying substantially the same image on at least two remote locations having a programmer device and a computing device as set forth above.

The invention, then, can be described as a method for communicating between at least two remote locations so as to enable coordinated display of a physiologic waveform and pointer/cursor information which preferably has these steps:

capturing pointer/cursor information regarding a location on a display screen for each said pointer/cursor, redacting image data from a video display buffer based on said pointer/cursor information so that the remaining video buffer data represents a display sans said pointer/cursors reviewing the redacted video image buffer so as to locate any changes since a last review, creating an index of information describing which locations in said video buffer contain changed data since said last review, capturing representations of the images at the changed locations and storing this as data in a buffer, compressing the index and the capture buffer data, sending the compressed index and capture buffer data from one of said at least two locations.

Preferably, said pointer/cursor data is sent in said sending step. It can also be described as a method of communicating between at least two remote locations so as to enable coordinated display of a physiologic waveform and pointer/cursor information preferably having these steps:

receiving compressed index and capture data across a communication line from one of said at least two locations at a first of said at least two locations, decompressing said index and capture buffer data, swapping in information from said capture buffer data at locations in a video display buffer representing corresponding locations to those indicated in said index data so as to enable a display at said first location to display said changes.

A preferred form of the method includes in the step of receiving data representing pointer/cursor location on a display screen from said one location of at least two remote sites and a further step of displaying an iconic image of a pointer/cursor representing a pointer displayed at said one remote location in a location on the screen in said first locations indicated by the received representative pointer/cursor location data.

DETAILED DESCRIPTION OF PREFERRED EMBODIMENTS

It should be noted that several of the terms used within this document are peculiar to particular companies systems. For example, the term 9790 is the name of a programmer used for programming implantable devices produced by Medtronic, Inc and well known in this field. The 'Macintosh' or 'Mac' is the name of the operating system/user interface for Apple Computer company's computers. E C G and E K G are abbreviations discussed in the background section. Minix 8340 is a name for a particular implantable pacemaker produced by Medtronic, Inc.

Numerous terms are also employed which have common computer and communications industries meanings including, PC, meaning a small or "personal" computer, "application", "layer", TCP, RS-232, and other terms have their commonly used and known meanings also.

Figure 2:
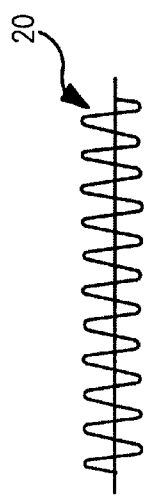
FIG. 2 is a simplified representation of any data communications system.
Figure 1:
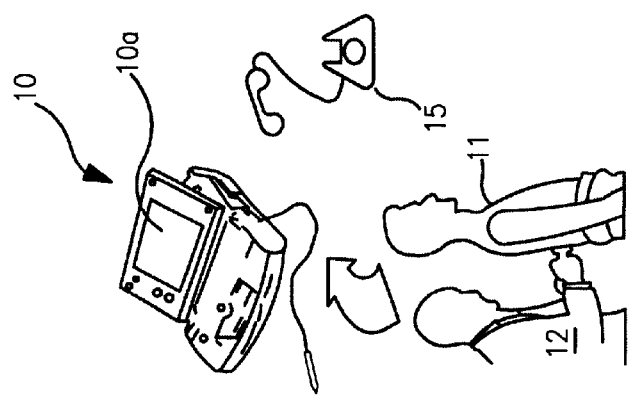
FIG. 1 is an overview of the "local" environment having a physician, patient, and programmer device present.
Figure 4:
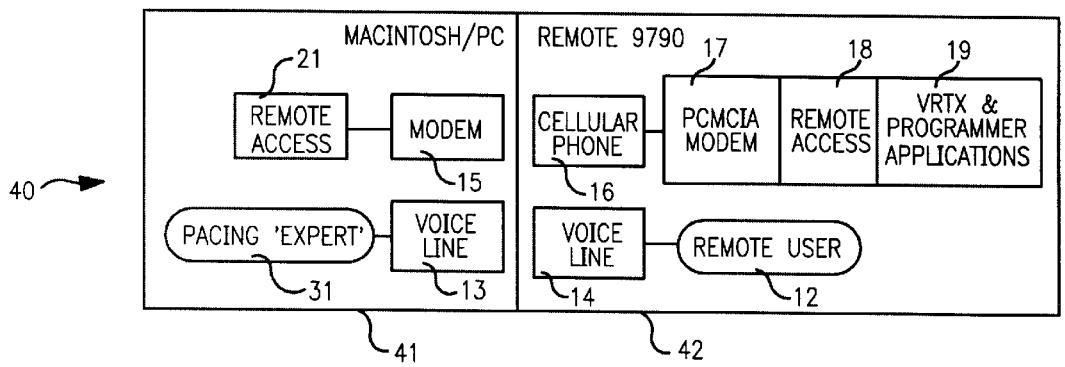
FIG. 4 uses a communications layer block diagram illustrating "MedConnect" layers and related communications layers in accord with a preferred embodiment of the invention.

In its broadest form, the invention operates in a system having at least those parts heuristically illustrated in FIGS. 1–3. In FIG. 1, a programmer 10 (a Medtronic 9790) operates as the local device having a display 10a and input mechanisms for use by a clinician 12 who may be examining a patient 11. FIG. 2 briefly illustrates that communication channels may include phone lines 20 to provide data transmission as well as voice communication between the device illustrated in FIG. 1 and the device of FIG. 3, a physician, company representative, or other expert one may be used the communications device 30. In both FIG. 1 and in FIG. 3, are device 15 and 32, respectively, which illustrate that an additional communications device and/or channel is useful for the best operation of inventive system. FIG. 4 illustrates in diagram form, a version of the same system 40 as was described with respect to FIGS. 1–3, as essentially of two parts, a part 41 local to the expert but remote to the clinician, and a part 42 local to the clinician but remote from the expert. In the preferred embodiment, connects between the pacing expert 31 and the remote user 12 via modem 15, 17 or any other type of modem. Here, a cellular phone 16 may connect to the modem instead of using wire connections as just another example of the realm of possible system communications components. Video and/or audio connections 13,14 may additionally be maintained to facilitate the communications between the user and the expert. With this setup, the data on the remote access system 21 at the expert's site can send and receive data, be in communication with the "VTRX" and other programmer software applications running at the remote user site. (VTRX is a particular kind of system like a DOS or Windows or OS/2 operating system from Microsoft or IBM, but it has some features for running applications in programmers not normally found in the other OS's).There does need to be some coordinating program, here called remote access 18 at the user site that is designed to understand the suitably configured data streams sent between the remote access program at the expert site and the data streams and programs that use them at the user site.

Figure 5:
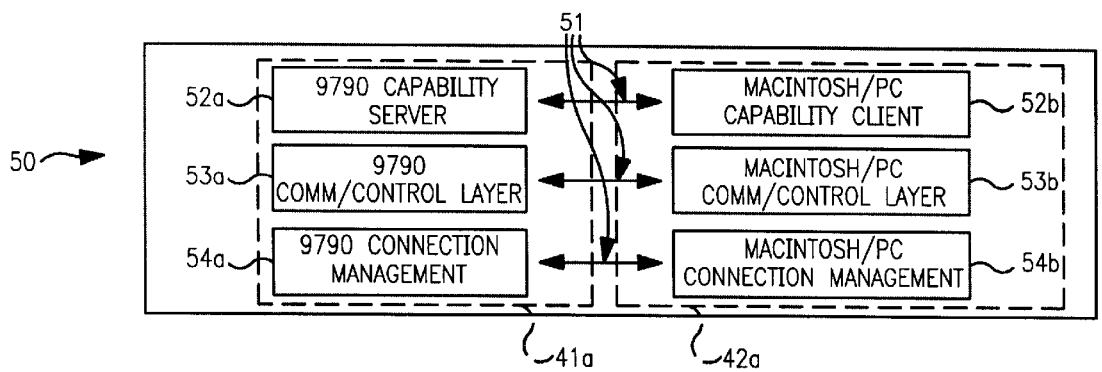
FIG. 5 is an alternative view of the communications interface illustrated in FIG. 4, expanding on the details of the communications layer depicted in FIG. 4.

It is important to note that there are various levels of communication required in order for the user accessible high level display programs in the remote access device 21 and the related programs in the expert device to be coordinated. In FIG. 5, the system 50 is illustrated having a logical facilitated communications link 51 between each of the operating layers of the displays at each location. For device 41a and device 42a, a software layer management connection 54a and 54b respectively, must be communicating in a cooperative manner. Additionally, a communications control layer 53a and 53b must pass the working information from the connection management layer to the capability layer 52a and 52b, in order for the cooperation to be accomplished.

Figure 6:
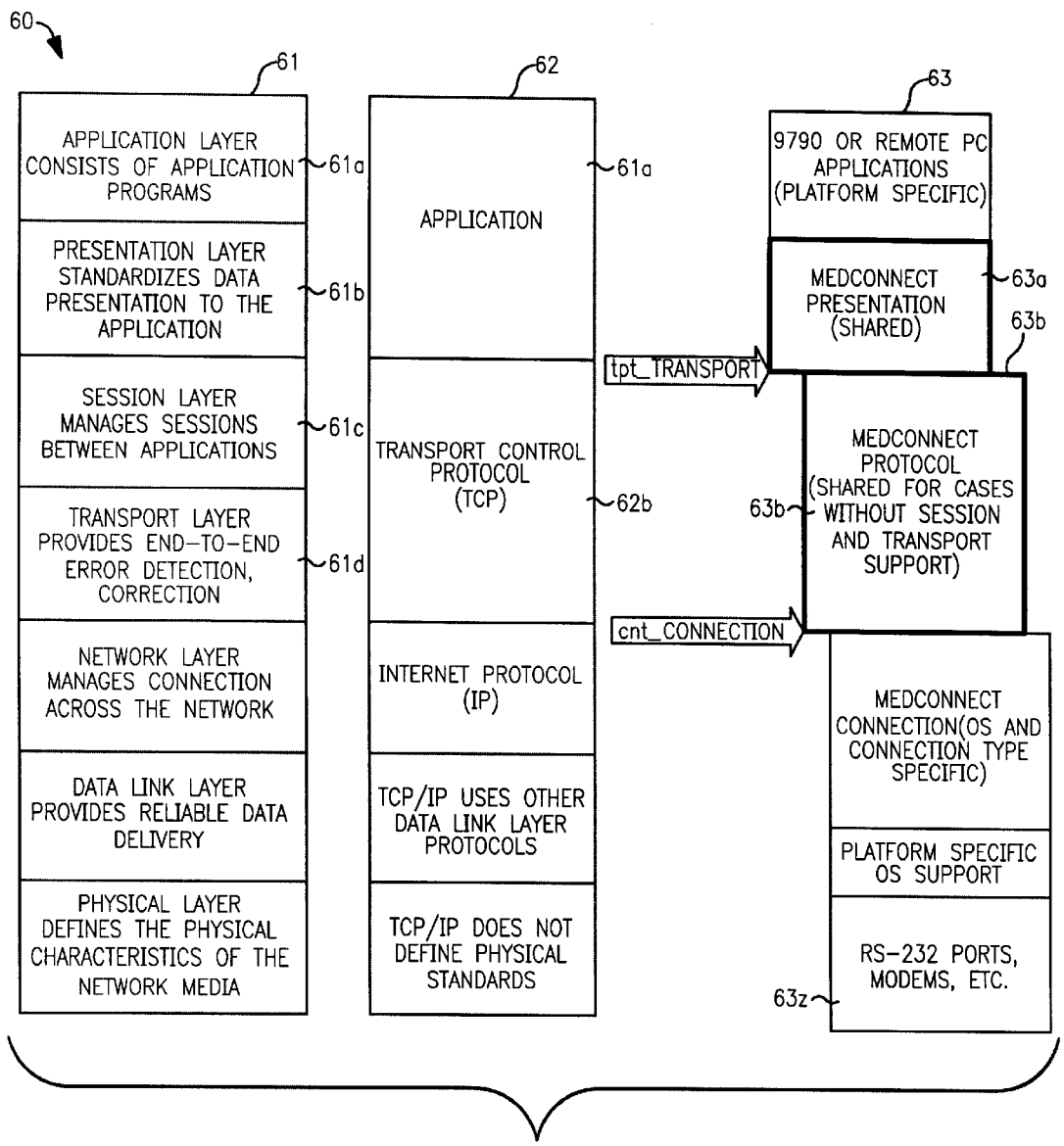
FIG. 6 is a stack diagram of communications and protocol layers providing an alternative representation of FIG. 5.

A more typical figure for explaining the interrelationships between protocol layers is in FIG. 6. Referring now to FIG. 6 it first must be recognized that the entire column for the preferred MedConnect system would exist at both the expert and patient sites. Remote access software at both sites is depicted in block 63. The columns to the left of the "Med-Connect" column depict mappings to other existing communications architectures that may alternatively be used or which may communicate with the MedConnect system. Blocks 63a and 63 together equate to the TCP/IP concept of an Application block 62 or the ISO/OSI concepts of Application layer 61 and Presentation layer 61b. Block 63b equates to the TCP/IP concept of the Transport Control Protocol or the ISO/OSI Session Layer 61c and the Transport Layer 61d.

Also, as would be understood by communications workers familiar with such diagrams, the column under "Med-Connect" in most embodiments names the layers of hardware and software from the user application to wires and back through which any data must flow. In other words, the application layer passes data through each layer beneath it and from one set of wires at layer 63z, back up into another identical column at the remote location to block 63 in the most preferred or MedConnect to Medconnect embodiment. It is also recognized that not all uses will be of the proprietary MedConnect protocol so the communication to applications in collumns 62 and 61 can also occur, although through different layers as shown in those collumns. Thus in one preferred form,it can be seen at 61 that a feature in the application layer (block 61a) of the expert system located remotely from the application layer in (the 9790 or similar patient local device) in column 63 must pass data on timing and location that survives numerous translations and communications down into the physical layer across the communications network and back through another physical layer to the remote application at the top of its collumn. Of particular relevance to the instant invention are blocks 63a, and 63b , which enable the coding and decoding of appropriate information to accomplish the specific inventive coordination tasks. Thus, the presentation layer 61b in the ISO OSI standard system on the right would contain the decoding and encoding software features necessary to accommodate layer 63a data, and if it did employ session data, it would have to coordinate with the connection layer 63b data in layer 61c and coordinate transport data through layer 61d. The lower layers would just carry the packets and physical signals and should, of course be coordinated in well known manners. However, in the TCP/IP case, the layer 63b could be eliminated as unnecessary. Also, if both systems had all the elements of the MedConnect system column, they would both need the layer 63b. To summarize, there must be a similar protocol stack in each location's system.

Figure 8:
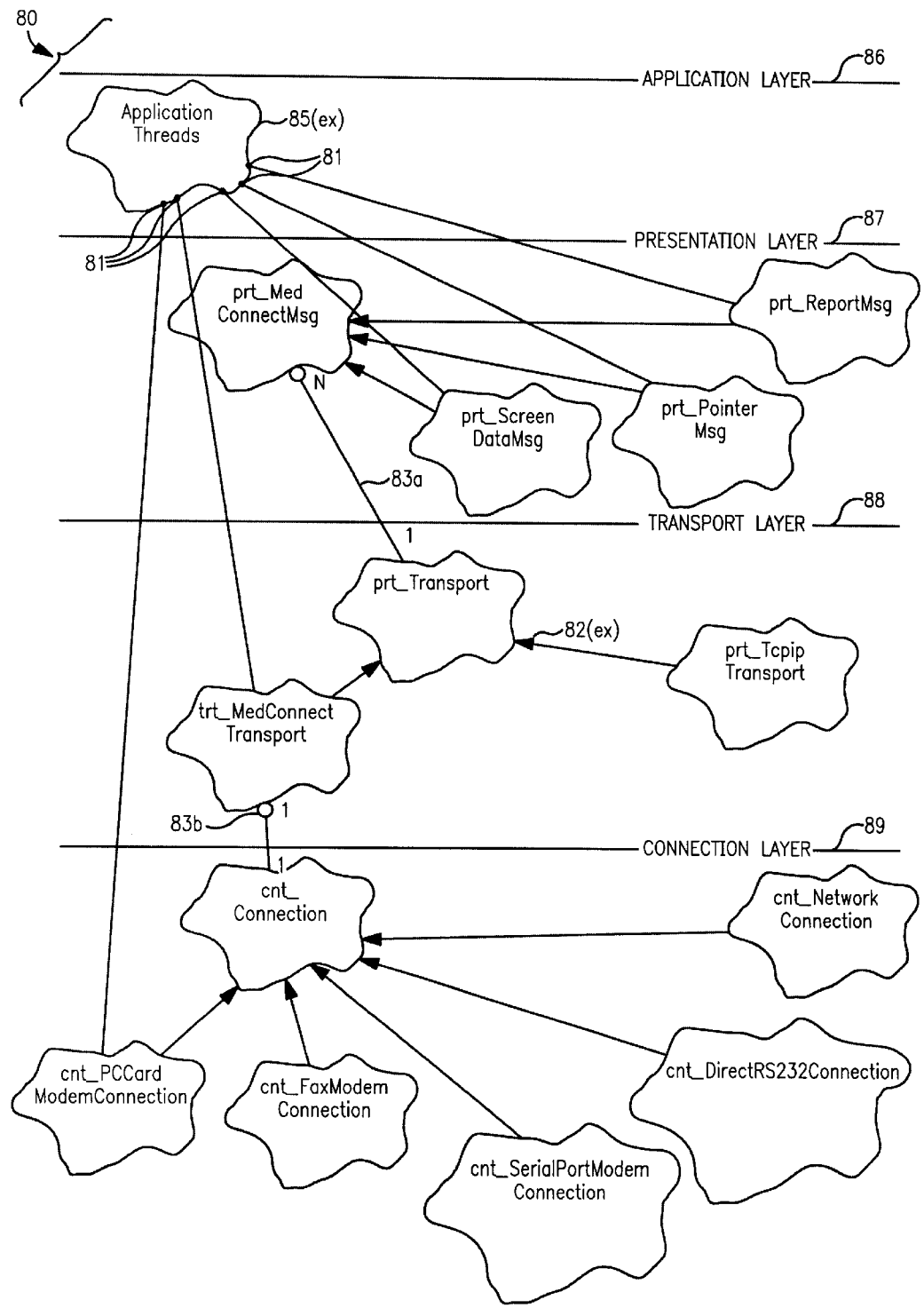
FIG. 8 is an alternative graphic representative illustration of the relationships of the communications linking arrangements displayed in FIG. 6.

Referring now to FIG. 8, this diagram provides an alternative view of one organization for the preferred embodiment communication layers from 86 through 89 at a location within one of our preferred embodiment systems. At the upper level, the application that provides the device functionality at the device site, say for example, enabling pacing system analyzer data to be monitored and used at an implant where leads are connected for testing to a programmer. The application software would control the display on the local screen within the application layer by using the data in the presentation layer 87. In this layer, the display or "prt" cloud 84 contains data used for location and other display functions, (color etc.,) and this data is communicated between the application and the cloud 85(ex by direct links 81 to these particular data values (prt_ReportMsg, prt_PointerMsg, and prt_ScreenDataMsg, among others which are not shown). Each piece or chunk of data for communication can be thought of as being placed into a buffer for formatting appropriately for enabling the communication of that data in the buffer. These buffers are combined into the data blocks or packets shown for example in FIG. 9b. These values are linked to the transport and connection layers as shown. In understanding this diagram of FIG. 8, recognize that the arrows indicate that the cloud doing the pointing is a subset of types that are represented by the general cloud type pointed to.

Application threads 85 exist on both the expert and patient local devices. This layer 86 is equivalent to block 63 in FIG. 6.

The applications 85 use the values in these components (e.g. prt_ScreenDataMsg, prt_PointerMsg, prt_ReportMsg) to format data communications messages between the Expert and Patient devices. These components are of a base type prt_MedConnectMsg. All these message types would be contained in the MedConnect Presentation block 63a depicted in FIG. 6

Details below the Transport layer line 88 relate strictly to communicating the data between the expert and patient device locations.

The tpt_Transport base type equates to the block 63b depicted in FIG. 6

The cnt_Connection base type equates to the blocks below cnt_Connection arrow on FIG. 6.

For specialized different types of communications media there are representations given (e.g. cnt_ . . . clouds pointing to base type cnt_Connection cloud 84c) each of which uses generalized abilities of the Base type.

Figure 9A:
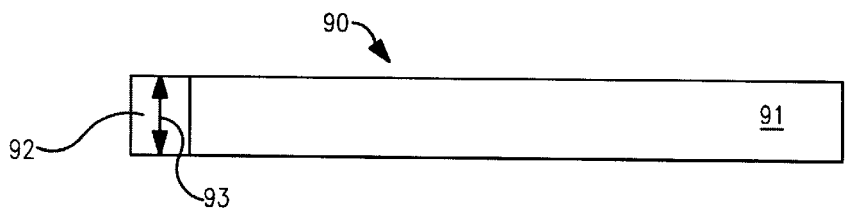
FIG. 9a illustrates an ECG display window which would be a single element on a display screen in accord with a preferred embodiment.

In FIG. 9a, an ECG display window 90 is illustrated, the height of the window 93 is constant throughout, and the widow itself comprises essentially two segments, an active portion 92 and a trailing portion 91. Only a small part of window 90 is actively receiving new data at any time in either the remote or local device. It is the nature of ECG wave form that only the leading edge is active, the rest of the display merely allows the leading edge to travel rightward along the screen. Therefore only the active portion needs to be maintained through coordination, since the display manufacturing software local to either system can simply redraw the element that was in 90 as it moves to the right in any of numerous well known ways. Thus, while the local device is receiving the actual electrocardiogram from the patient's attached electrodes, it is sending this data to the remote device as it also draws it on the local screen. The amount of data to transfer is very small since only the leading edge needs to be sent. The refresh rate will depend on how wide window 92 is in the preferred embodiment, the baud rate for data transfer(, the size and frequency of the data packets being transferred will affect the baud rate), the speed of the local computing and display device, and the resolution of the image.

However, given sufficient bandwidth, the entire ECG (or other physiologic data signal) display can be transmitted continuously.

Figure 7:
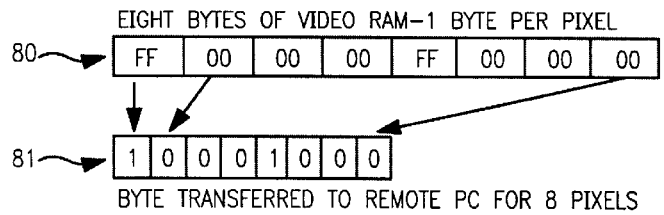
FIG. 7 is an illustration of a two color (8 bytes to 1 byte) video data compression scheme used by a preferred embodiment.

FIG. 7 details a data transfer configuration employed by a preferred embodiment, and an explanation of how it works will help to indicate how the data of a screen display is transferred. When used for the ECG display area, we found that the simplest way to transmit a lossless physiological signal was to limit the display to a two color display, such as Black and White. In doing so we could transmit the entire changed area of the screen representative of the physiologic signal that exists at the moment by only transmitting those very small portions that change. Thus the entire line of ECG data could be transmitted in a very short chunk of data. The video RAM (Random Access Memory, a term with its common industry connotations), is divided into indexed area representations each of which indicate whether and what pixel configuration is lit, colored, and so forth. These typically require a full byte for an 8 color pixel and significantly more for any more enhanced pixel representations (like 16-color displays for example). By limiting ourselves to two colors, the pixel is either lit or not lit, thus inherently allowing for a quick compression to a one or zero representing the pixel. Also, by using run length encoding, every byte of identical data becomes a single bit in the transmitted data stream. So referring back to FIG. 7, we have divided the video RAM index 80 into 8 bytes for the area under consideration. If there is a change in any of these areas, a corresponding bit is set in the data word 81 which will be sent to the remote location indicating which of the areas of the index have changes in the display at the location known to be indicated by that index. Accordingly, the program at the receiving end will expect, for this example, the first and fifth sections need to be updated at its location and will look to the data in the remainder of the data packet or packets being transferred which relate to this index byte 81 for details about changes in those indexed locations. Typically, the X,Y location of each byte will be kept in a look-up table in both locations so the machines at each location can interpret this data as it comes in. The area of the screen which contains the display of the non new portion of the ECG will not be indexed, since it will be computed as the follow through of the leading edge information always received in each information transfer that has a new index byte, in the preferred embodiment.

Figure 16:
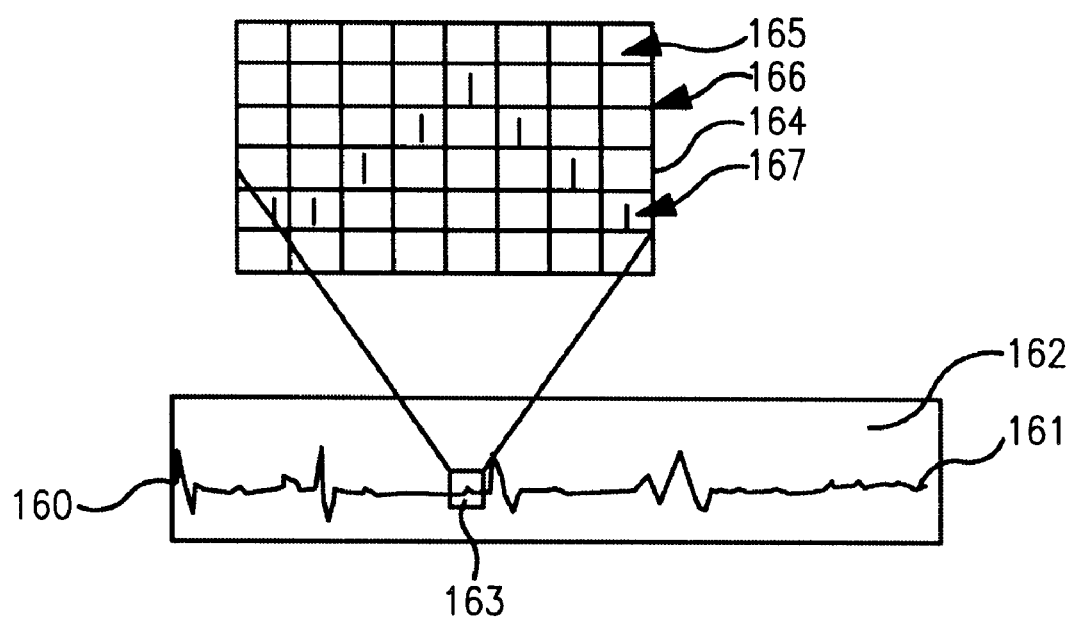
FIG. 16 is a heuristic diagram having a blown up portion illustrating the arrangement of video RAM data memory organization relative to an area of video display.

In general, continuous screen capture is done by repetitively examining video memory, comparing it to the last known state of video memory, and then sending only the data representing the rectangular regions where data has actually changed on the screen. The video memory is read directly and the software screen compare routine finds the changed rectangles. We employ a specific algorithmic process to accomplish the search for changed rectangles set forth in detail in the Appendix, hereby incorporated by reference. The result of using this preferred program (although any one which accomplishes the result would suffice)is illustrated with reference to FIG. 16, wherein a portion of a videodisplay representing the ECG signal display 160 is shown having a one color physiologic waveform line 161 and alternate color surrounding space 162 drawn thereon. (The use of this program or a similar one could also be appied to the rest of the screen but our maost pressing concern is for rapid updating of the physiologic waveform data so this is done separately, preferrably). The rectangle area 163 is represented by an 8 by 8 area of memory 164 having a block set for each line color and blank for each background color space within the rectangle 163. A row 164 corresponds to row 80 in FIG. 7, and the compression from the FF rrepresentation to a single bit is already shown in this illustration.

Using the compresion scheme set forth here the changed data is then run-olength encoded, packaged with appropriate protocol and sent to the remote device through the various layers as necessary.

In the preferred embodiment we also remove any screen pointers from a screen to be sure that they do not appear as part of the signal data before doing the screen capture operation and then with the pointer data there can be replaced, on top of the display of the screen data. Thus the video RAM has an image of the screen without any pointers drawn on it, and the X,Y screen coordinate location allows the operating program to draw the pointers/cursors on the screes where appropriate, painting over the background or any other feature at that X,Y coordinate.

It should be noted that other data compression methods, such as run length encoding may be superimposed upon any screen capture data to minimize the amount of data necessary for transfer for large screen areas that are totally one color, or an other, or are a simple stippled pattern.

Figure 9B:
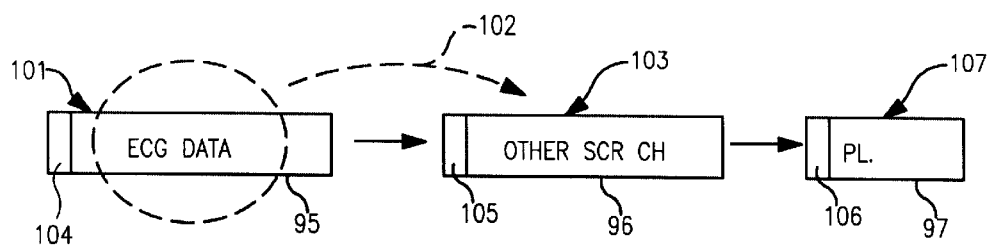
FIG. 9b illustrates three data packets that may be organized as shown for preferred embodiments of the invention.

FIG. 9b is a representation of data being communicated between the remote expert and patient sites, having, as shown here a train of data packets 101–103 each organized to have its own unique identifying header 104–106, respectively. Preferably it is organized as follows. ECG Data 95 is treated as its own data type and sent separately in its own packets. ECG Data 101 can be treated 102 (dotted line) as Other Screen data 103. Other screen data 103 is raw screen pixel data with no special features identified, and in the preferred embodiment will contain only the changes made from the last time the screen was updated. Pointer Location data 97 is communicated between expert and patient sites.

Figure 15:
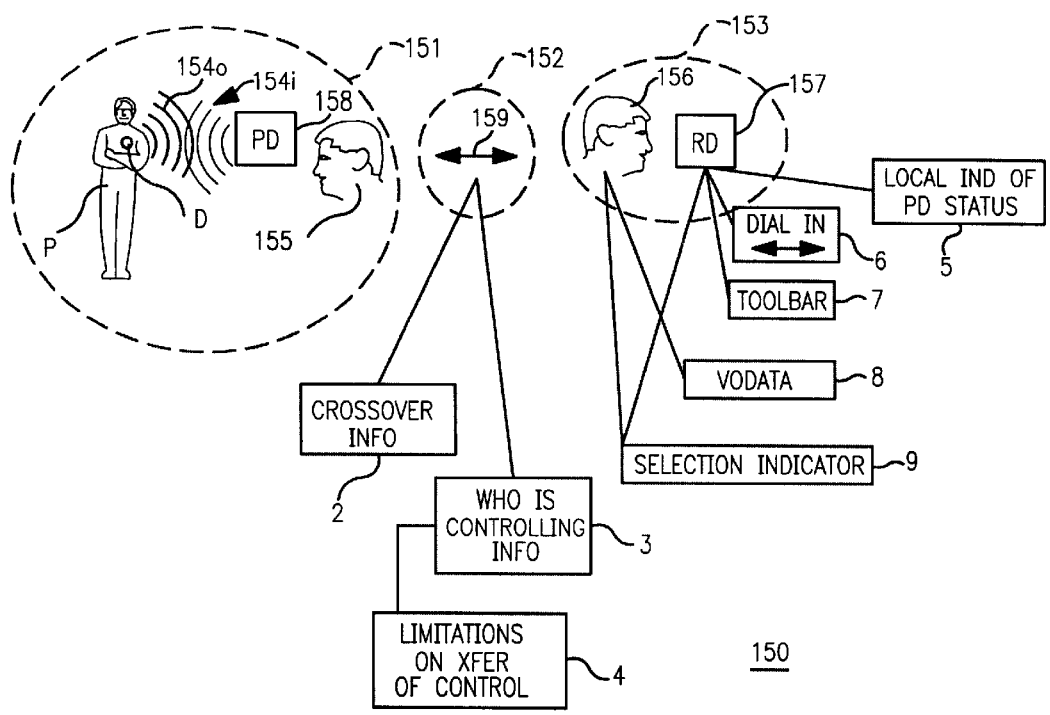
FIG. 15 is a heuristic diagram of system components and their interaction in accord with a preferred embodiment.

In FIG. 15 a more detailed representation of the system 150 than was available in FIGS. 1–3 illustrates the system in a more interactive manner. Essentially the system comprises three parts 151,152, and 153. In part 151 is a patient P with an implanted medical device D capable of transmitting information via RF or H field waves 154o and receiving information via waves 154i. The local computing device PD 158 provides this wireless communications pathway between the implanted device and the local actor 155.

In section 152 the communications channel 159 is merely illustrated by an arrow. The important pieces of information which transit this mechanism 159 are cross over information 2, identity of the controlling system (block 3), whether it is in section 151 or section 153, and what limitations there are on the transfer of who is controlling (block 4). In the cross over information block 2, timing information and size and location information for the leading edge of the E C G display as well as information relating to the current location of the pointer on each local screen.

In section 153 the remote expert 156 operates the computing device 157 connected through section 152 to the computing device 158. As previously indicated expert 156 may also have voice or video over data connections to the section 151 area, here indicated by block 8. A selection indicator block 9 is shown here to indicate that at this moment the remote expert 156 controls the pointer on the screens of both the R D device and on the P D device. Each one of these boxes, except for 6, and 7 which will probably remain constant throughout large portions of each communication, and block 8 which is Voice Over data being carried directly through aural communications between the actors 155 and 156, will probably have some data being transferred in each packet or group of packets of information being transferred between the sites.

To provide a complete understanding of the system we must refer to the screen displays.

Figure 11:
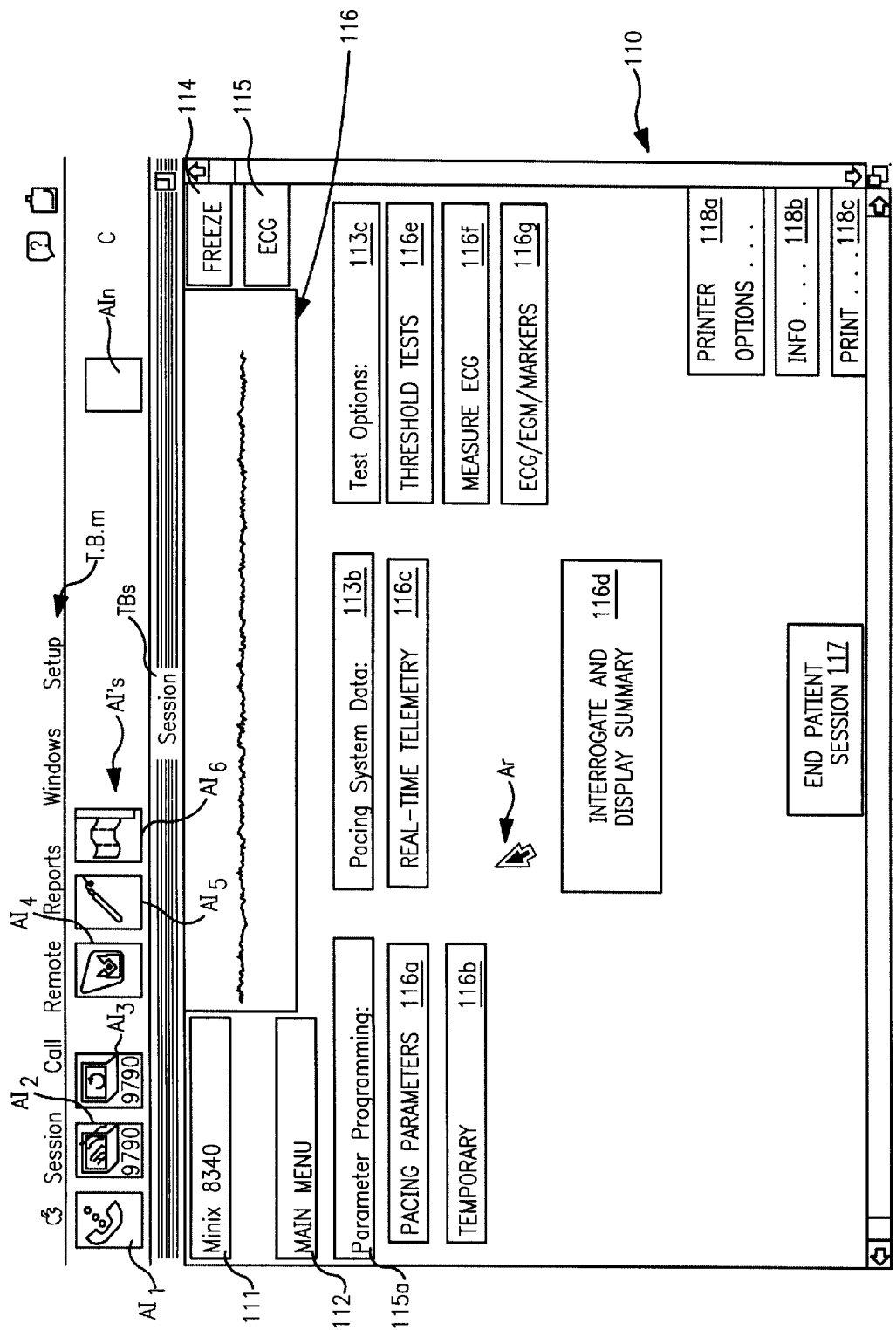
FIGS. 11–14 are illustrations of screen displays in accord with preferred forms of this inventions.

Referring now to FIG. 11, a typical PD (Patient site located Device) display screen 110 is illustrated as it would appear on the remote expert's screen. As in most computing devices, there currently exists a background tool bar main menu T.B.m. For this invention we have determined that it is advantageous to use a number of active icons here labeled AI's 1-n. In this display the icon AI1 opens a phone directory when 'clicked' or activated by a cursor, that may allow interaction with the communications programs, or just monitoring of the connection with the expert's device. AI2 and AI3 provide indications of how often the updates occur between the remote and local screen displays, and can be used to change that frequency in preferred embodiments. The next two, AI4 and AI5 are icons which will be active depending on whether the expert indication pointer is active (AI4 would be highlighted in that case) or whether the expert's enabling pointed would be active, here shown as an icon of a light wand. AI6 indicates the print function, and the designer can include whatever others are desired for a given system set up. The title bar TB, shows that the PD is engaged in a session, or prepared to run a session.

Figure 14:
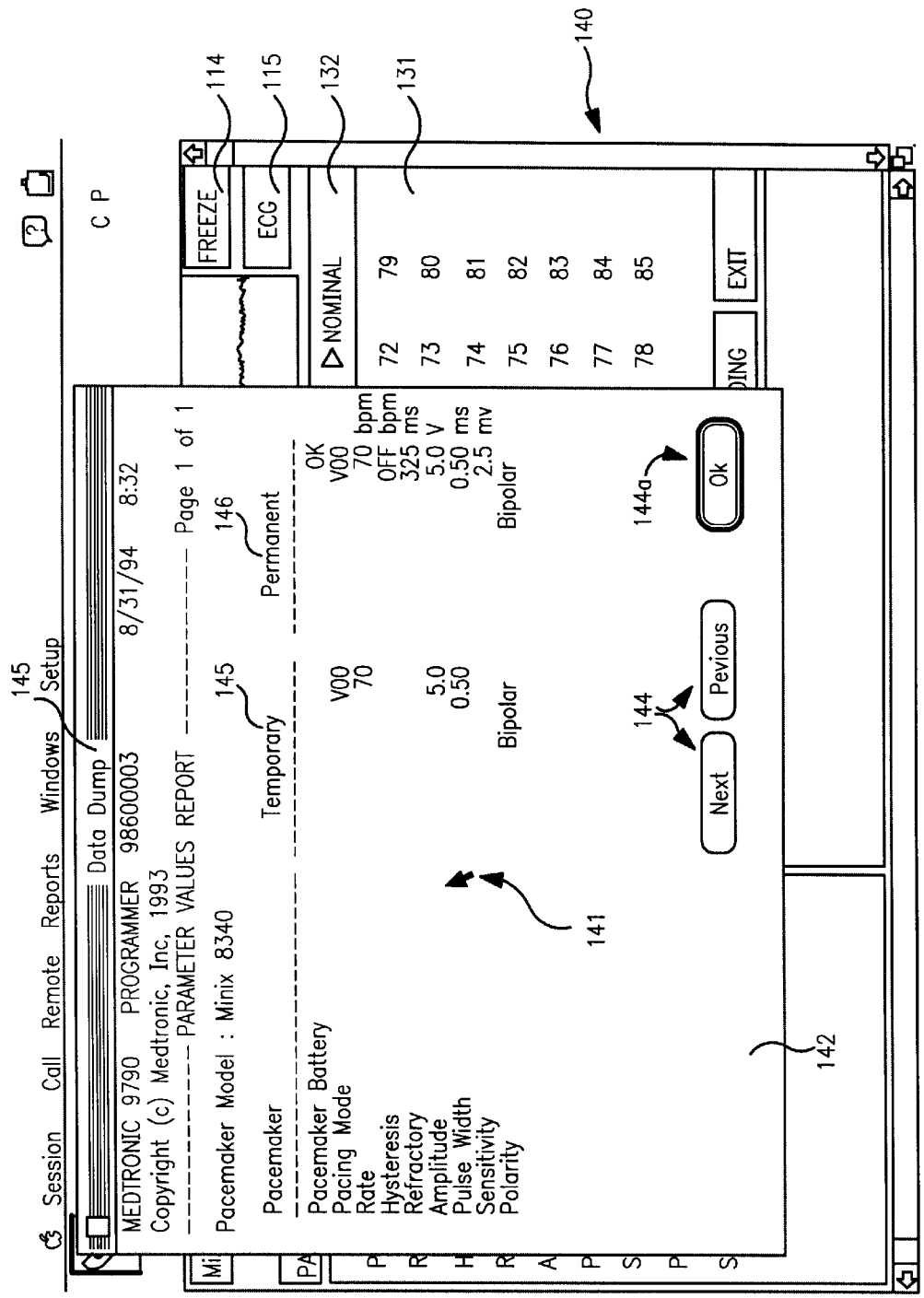

Note there is an arrow Ar, which the expert user has only on his screen, and does not appear on the screen of the patient located programmer. This arrow can be used by the expert to perform auxiliary tasks in background like receiving a data dump (as illustrated in FIG. 14) or for consulting an expert system resident on his computing device or other system on his computer, while at the same time the expert may continue to monitor the PD location.

Here we also have a number of other active buttons on the screen appropriately labeled with their functional title 112–118. For example, the implanted medical device in communication with the local PD here is indicated at site 111, as a Minix 8340 a type of pacemaker. The serial number or other unique identifier could of course be displayed also if desired, perhaps by clicking on the button labeled Minix 8340. This screen 110 shows the main menu 112. Three sections 113a–c are present which can report data relative to those areas or enable options under button 113c, as well. Using button 116f, for example, the ECG screen area 160 would become active and show the real time ECG form the leads on the patient's body or from the telemetered out information from the implanted device or from a pacing system analyzer if such a device is active and attached to the programmer.

Figure 12:
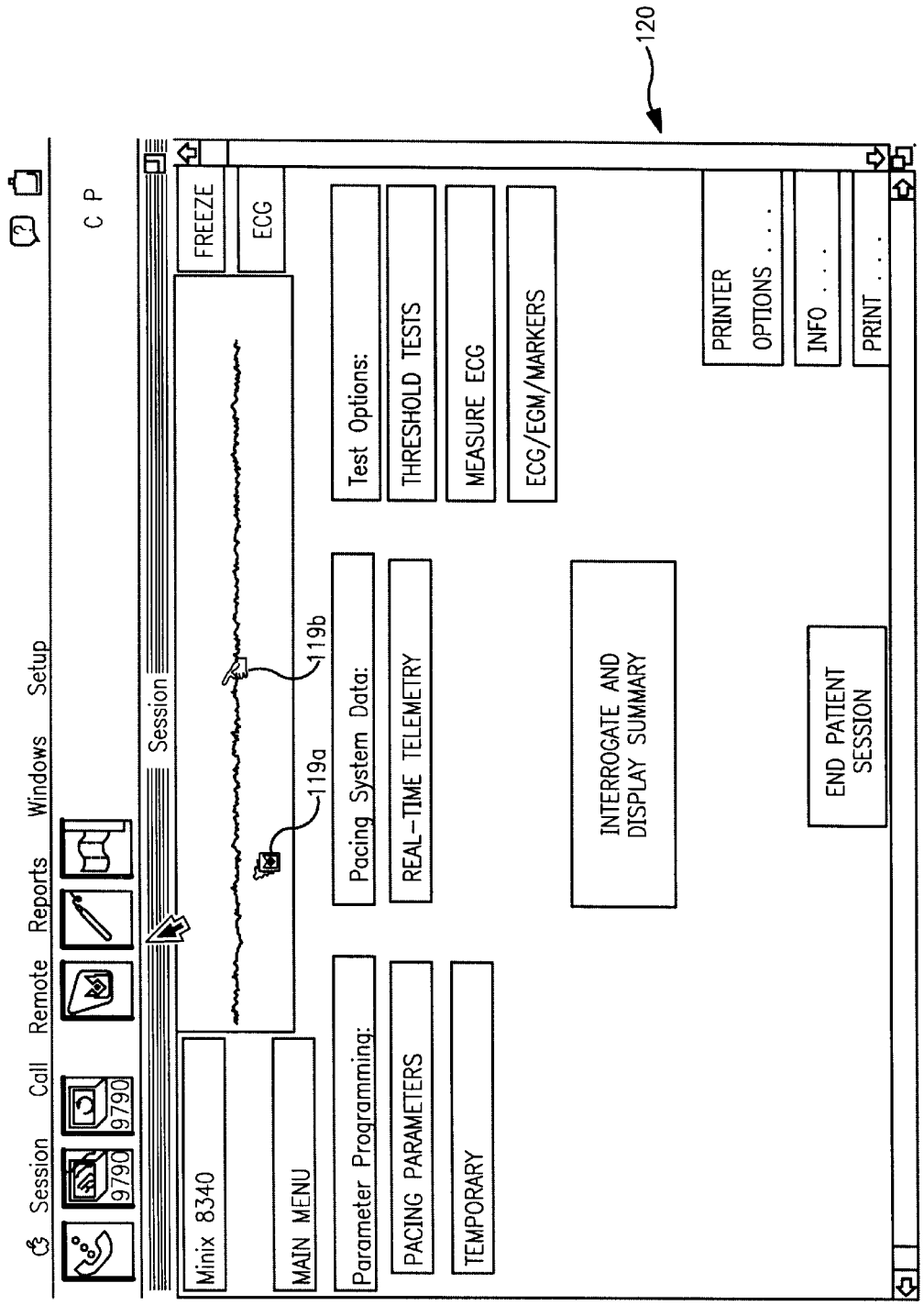

In FIG. 12, the expert and the local user can be seen to both have their controlled icons, 119a and 119b, respectively, concentrating on a portion of the ECG display, the expert's pointing to the left of the patient local user's.

Note that the icons for each location are different and unique to that location, even though they may be displayed remotely. This reduces the potential for confusion and enhances accurate and fast communication of knowledge of the situation between the remote users.

Figure 13:
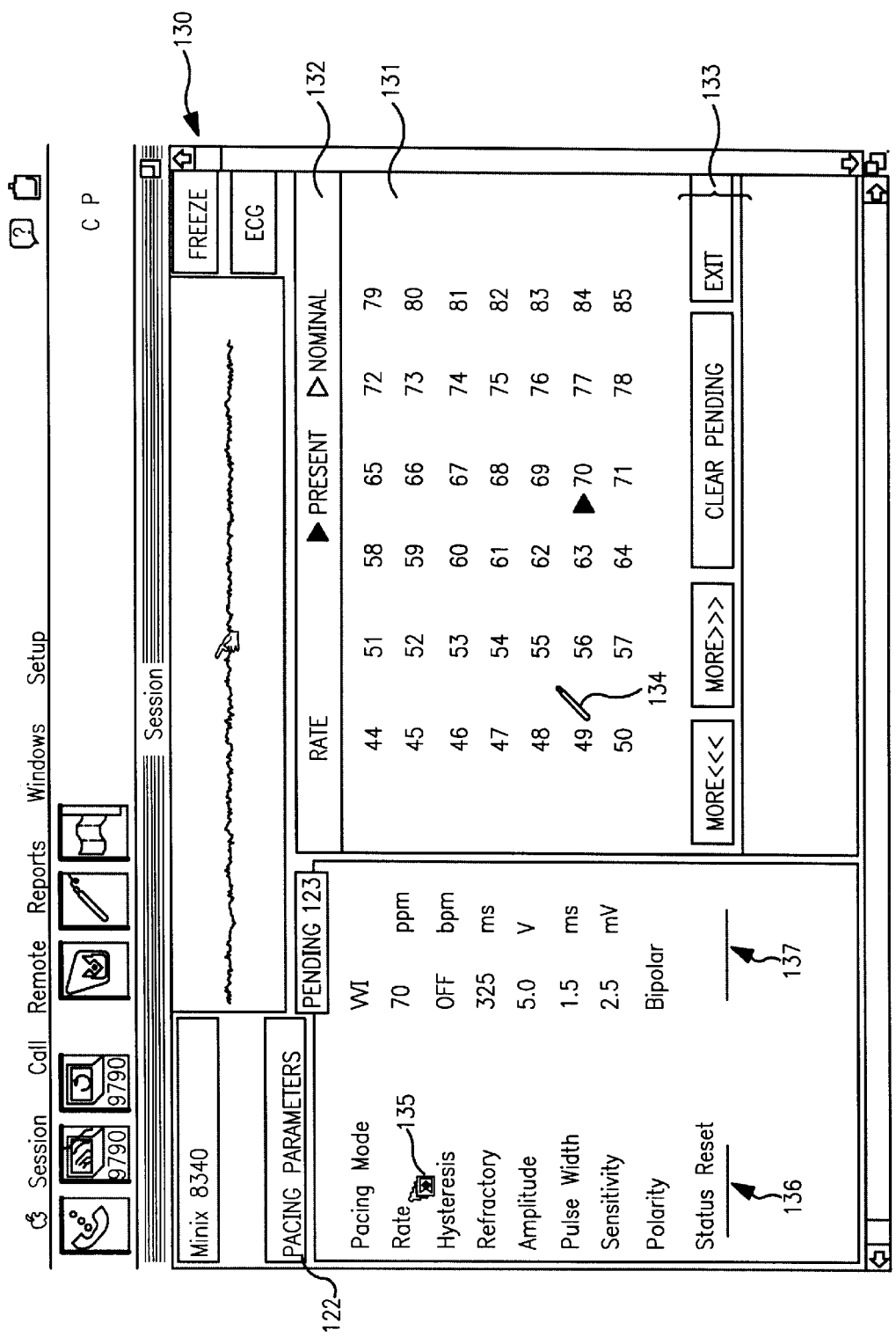

On screen 130 in FIG. 13, the menu option displaying pacing parameters 122 is present. It was made active by the expert using his button 135 at the location shown. The expert would then have switched pointers and activated the active button press at the patient local site using indicator 134, indicating a rate of 49 bpm in area 131. Depending on the embodiment, the user may have to activate this rate by moving his own patient local button to this location shown by the expert at 134 or the expert could activate the local programmer if desired. The ability to allow a local expert to actually run the features of the programmer rather than asking the patient local person to do what the remote expert indicates is a matter of preference, and it may be considered better in some situations to keep the remote expert from having the power to modify local programming or it may be considered essential to disallow such distant control.

For the purpose of being complete, note FIG. 14 which has a separate window superposed over the background window of FIGS. 11–13. This merely indicates that normal functionality of multithreaded or multiprocessing systems may be maintained in a background mode at either site. The large white space area displays the data dump that informs the expert about the system and the patient he is communicating about. This data dump screen need not be displayed at the patient site, as in the preferred embodiment. To keep this data dump display (or any other local display) completely local, we handle the covered area of the screen in a manner similar to the way we handled the screen area covered by a pointer. That is to maintain the buffer data for the underlying screen separately from the data for the local-only display in elation to a set of X,Y registers that locally maintain the reference to the appropriate screen location. The data in the local-only buffer is then "painted over" the appropriate screen area in accordance with the display routine for the local operating system.

Here the activating pointer or cursor 141 is an arrow, and if it is clicked when located over one of the buttons 144 or 144a, that function will be run by the computer supporting this display 143.

To reiterate and further explain how this pointer coordination is accomplished, we can use a set of registers with the X,Y coordinates of the pointers for both machines at both locations. When any data is received from a remote location, and there is any indication of a pointer move in that data, the registers will be compared with the incoming data for the relevant registers and if a change is found, the program will accommodate it in accord with the appropriateness of the action and by moving the cursor related to that changed data at the local screen. Flow charts in FIGS. 10a and b clarifies this matter. In a preferred embodiment we used a standard O S/2 programmer window implementation, the drawing screen driven by the client window procedure and any re-drawing of all or parts of the window is done automatically when the client window procedure receives a WM_PAINT message from the system. (OS/2 is an operating system for IBM corporation computers). This WM_PAINT message used by OS/2 indicates that all or part of the window is invalid and needs to be redrawn. In our implementation, the screen drawing is driven from the individual application and not from a central procedure. This makes it difficult to restore the screen image under the second pointer as it is moving across the screen. A user touch screen may also be implemented and the pointer may be moved by a remote pointer message received from the remote PC if a remote mouse move is received from the remote PC the programmer will change the icon's pointer image to the remote PC representation and then move the pointer to be coordinates defined in the mouse move message. Moving the pointer at the programmer will be ignored and a pointer message will be returned to the remote computer PC with the Coordinates of the screen position being touched at the programmer site.

Generally then, a single pointer can be viewed and used by both the expert location and the programmer. It should be noted that the pointer on the 9790 programmer is touch screen activated. The pointer/cursor is displayed as an icon. It is coordinated, transferred, and displayed separately form the screen image. The icon is removed from the programmer screen, the screen, with the icon removed is what is captured, and the pointer-icon data then is painted over this screen. Messages relating to the data about the pointer/cursor icons must be sent back and forth between the two remote systems when either a touch-screen event occurs on the programmer or the user selects and moves the pointer/cursor icon(s) at the remote expert device. This is done with an input hood which monitors system messages for touch screen or pointer event messages. If a pointer/cursor activation event occurs, the X,Y coordinate is compared to the previous event saved at both sites for that pointer. If the X,Y coordinates are different, the pointer-icon displayed is moved to the new location and a message is sent to the remote device which allows the remote device to do the same. The pointer-icon representing the programmer is then displayed on both systems telling both users that the programmer was the last to move the pointer. This will display the effect of dragging a pointer icon at the remote location, when it is dragged at the local location. In one preferred embodiment, the programmer user's movement of a pointer icon takes precedence over that of the remote user and discards remote user commands if they are received while the programmer user is manipulating his local icons. This assures stable operation at the local site, allowing the physician at the programmer to maintain control to enable his rapid response to occurrences at the patient.

Figure 10A:
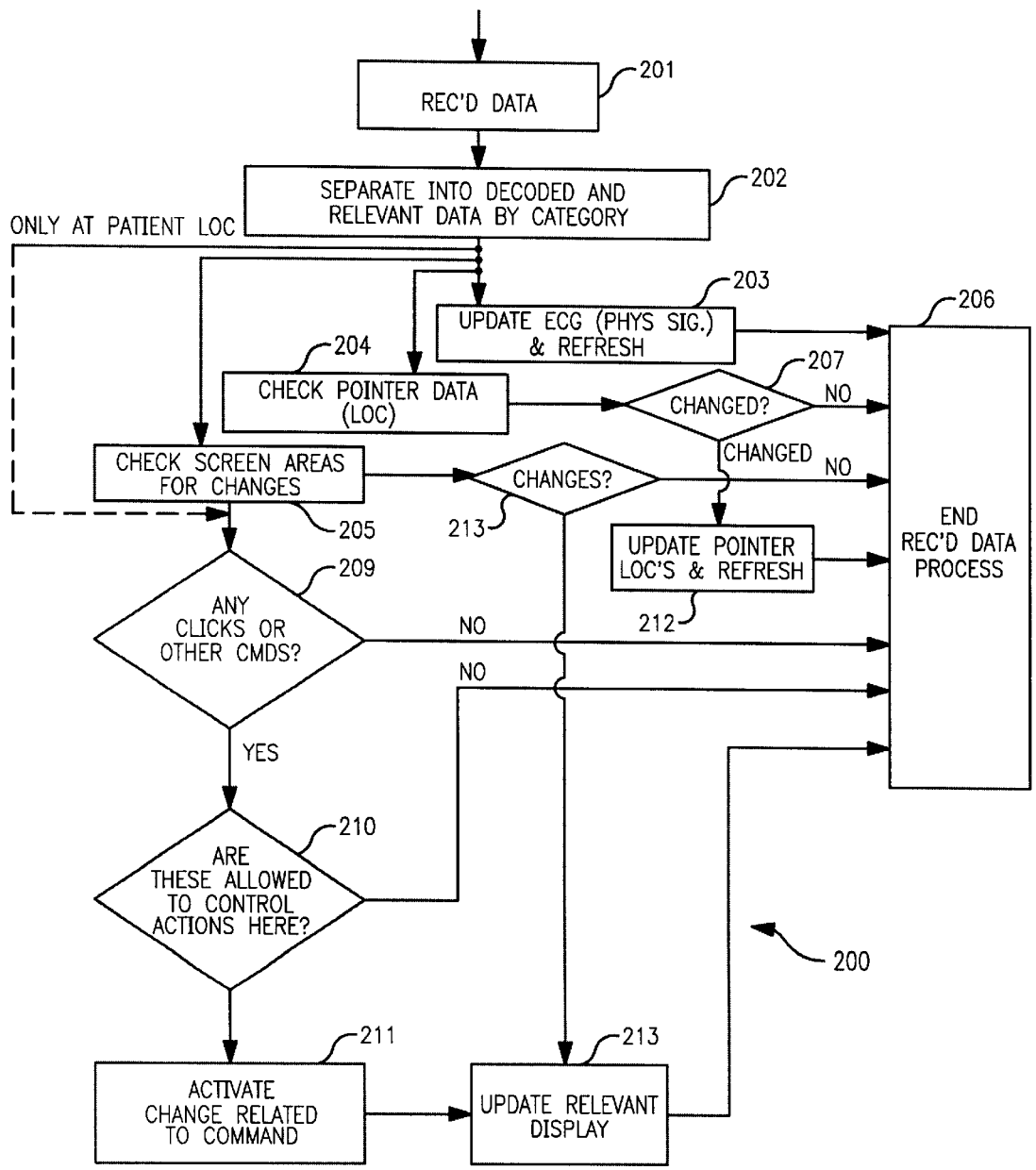
FIGS. 10a and 10b are block diagrams illustrating how program controls provide coordination between remote and local ECG data.

Referring now to FIG. 10a, the operation of either system to a remote command or screen change is outlined in flow chart 200. The incoming data is received 201, and separated into it's component parts of relevance in step 202. For example, the ECG portion of data in block 95 (From FIG. 9) is forwarded without it's header to step 203, and the process of updating the ECG or other physiologic signal waveform is accomplished. The pointer data from block 97 is sent to the process performed at step 204, and if no change is found 207, nothing further is done with that data. Likewise, the screen data areas are checked for changes (steps 205, 213 and updates of the relevant changes are made (step 213). If command information is received, it is transferred to processes at steps 209, 210 which determine if activation of these commands is appropriate, then the appropriate activation occurs, step 211, and then the display is again updated as needed 213.

Figure 10B:
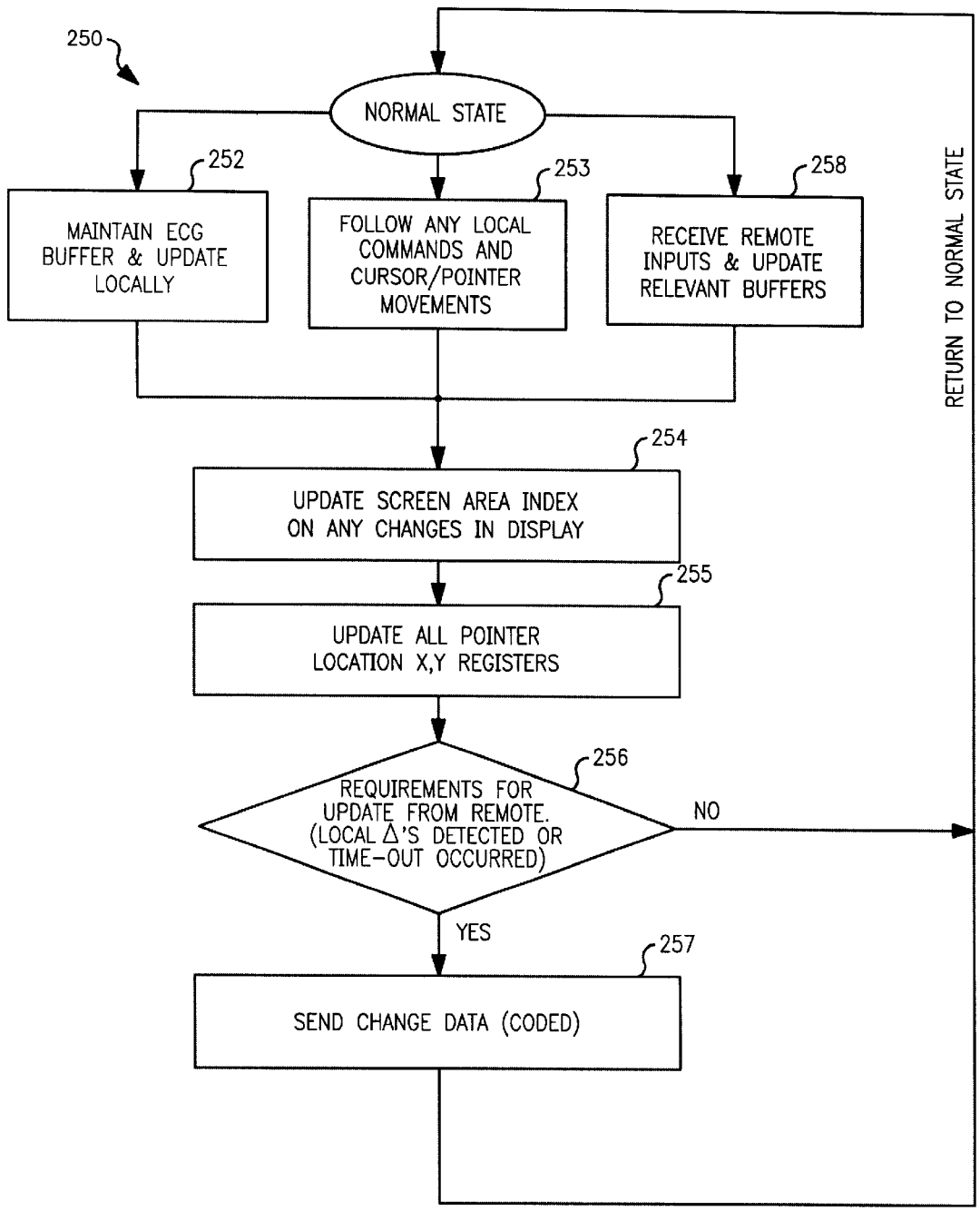

In FIG. 10b, the local control program steps that monitor and send out changes needed to be noticed by the remote system is outlined in flow chart 250. In the normal state, the operating system program is monitored such that the ECG buffer is maintained and locally updated 252. Any local commands initiated by pointer/cursor icon activation and movements of these pointers are kept track of 253, and any remote inputs related to any of these just mentioned data buffers may be received 258. A part of the inventive application program will then update all screen area indexes with the information from steps 252, 253, and 258, in step 254, in accord with the detailed description above. A separate portion of this program will maintain and update the new pointer/cursor locations in step 255 so these can be painted over the display without affecting the underlying display screen buffer. For local only information regarding the screen display, the same manner of operation is maintained as for the pointer locations. A part of the monitoring program performs step 256 which checks to see whether there have been any changes locally that need to be sent to the remote system, or simply sends the relevant buffer information on the occurrence of a time-out, if preferred. The relevant data is then packaged and sent 257 and the system returns to the normal monitoring state.

While it will be apparent to the reader that many adaptations may be made of this disclosure, it is only limited by the following claims.

APPENDIX

```
/* These three code fragments have been excerpted from actual code
files. They are presented here to illustrate a preferred embodiment
Screen Capture processing proceedure for finding changed areas of screens and
allowing for compression of video RAM data which can then be sent to a romote
location without loss of waveform fidelity*/
/* Main screen processing loop */
void
mnt_ScreenTransfer::threadFn()
{
    NG_TRACE_FUNCTION();
    unsigned int    index;
    int             minx, maxx, miny, maxy;
    int             new_minx, new_maxx, new_maxy;
    int             x, y;
    unsigned int    checked;
    bool            doneCheckingScreenWorth;
    unsigned int    lastLeftOffIndex = 0;
    prt_ScreenInfo* p_screenInfo;
    DATETIME        dt;
    mnt_Ulong       byte_length;
        /******** debug collection ********/
        /* open a file for debug collection */
        if (v_debugOn) {
        p_v_ScreenFile = fopen("SCREEN.DAT", "w");
```

APPENDIX-continued

```
            fclose(p_v_ScreenFile);    /* discard contents */
            p_v_ScreenFile = fopen("SCREEN.DAT", "w");
        }
    /********** end debug collection *********/
try
{
    // printf("The ScrnThread is executing.\n");
    p_screenInfo = new prt_ScreenInfo;
    v_screenThreadIsActive = TRUE;
    //tbd add to main the call to declare time-to-become-inactive
    while(v_screenThreadIsActive)
    {
        doneCheckingScreenWorth = FALSE;
        DosSleep(500L);
        // Check to see if there is a change in environment
        // For example, maybe color was turned off
        checkEnvironment();
        screenCapture();
        screenCompare();
        /********** debug collection ****************/
        if (v_debugOn) {
        // %4d means 4 places of decimal, %2x means 2 places of hex, % means an output
        // Note to output that a screen capture/compare was done
        fprintf(p_v_ScreenFile, "%.2d:%.2d:%.2d.%.2d screen capture/compare\n",
                dt.hours, dt.minutes, dt.seconds, dt.hundredths);
        fflush(p_v_ScreenFile);
        // In order that debug file does not grow indefinitely, close after
        // two minutes of collection.
        DosGetDateTime(&dt);            // Get Date & Time
        if ( (dt.minutes - v_dateTime.minutes) > 2) {
            fflush(p_v_ScreenFile);
            fclose(p_v_ScreenFile);
            v_debugOn = FALSE;
        }
    }
    }
    /*********** DEBUG CODE COLLECT END **************/
    // Find Rectangles and send
    while (!doneCheckingScreenWorth)
    {
        index = lastLeftOffIndex;
        y = index / v_bytesPerRow;
        x = index - (y * v_bytesPerRow);
        minx = -1;
        for (checked = 0;checked < v_screenSizeInBytes;checked++)
        {
            // Check flags until we have a rectangle to send.
            if (v_screenChangedFlagBuffer[index])
            {
                // If we don't have a rectangle yet set one.
                if (minx == -1)
                {
                    minx = maxx = x;
                    miny = maxy = y;
                }
                else
                {
                    // Check the x and y gap spacing to see if we can include
                    // this in the current rectangle.
                    if ((x >= minx - v_gapAllowedX) &&
                        (x <= maxx + v_gapAllowedX) &&
                        (y >= miny - v_gapAllowedY) &&
                        (y <= maxy + v_gapAllowedY))
                    {
                        // Determine the size of the new proposed rectangle.
                        // We will not set this as the current rectangle
                        // until we know that the area is not too large
                        // for a single message.
                        new_minx = minx;
                        new_maxx = maxx;
                        new_maxy = maxy;
                        if (x < new_minx)
                        {
                            new_minx = x;
                        }
                        else if (x > new_maxx)
```

APPENDIX-continued

```
            {
                new_maxx = x;
            }
            // Since we are advancing in the y direction and we don't
            // allow wrapped rectangles. We only need to adjust maxy.
            if (y > new_maxy)
            {
                new_maxy = y;
            }
            // Is the proposed block too big for a single message?
            // Note that following doesn't work if right side set to less than max
            if (((new_maxy - miny + 1) * (new_maxx - new_minx + 1)) > v_maxSingleMessageSize)
            {
                /******* debug collection **************/
                if (v_debugOn) {
                    /* %4d means 4 places of decimal, %2x means 2 places of hex, % means an output */
                    fprintf(p_v_ScreenFile,"          block-too-big test, %6d <= index%5dx%5dy\n",
                        index, x, y);
                    fflush(p_v_ScreenFile);
                }
                /***********DEBUG CODE COLLECT END **************/
                // Send the current block, and set an index
                // to remember where we left off.
                lastLeftOffIndex = index;
                break;
            }
            else
            {
                // Make the current block equal to the proposed block.
                minx = new_minx;
                maxx = new_maxx;
                maxy = new_maxy;
            }
        }
        else
        {
            // If we went too far in the y direction,
            // send the current block, and look for the next
            // block where we left off.
            if (y > maxy + v_gapAllowedY)
            {
                /******* debug collection **************/
                if (v_debugOn) {
                    /* %4d means 4 places of decimal, %2x means 2 places of hex, % means an output */
                    fprintf(p_v_ScreenFile,"          gap test\n");
                    fflush(p_v_ScreenFile);
                }
                /***********DEBUG CODE COLLECT END **************/
                lastLeftOffIndex = index;
                break;
            }
        }
    }
    // Advance to the next coordinate.
    x++;
    if (x >= v_bytesPerRow)
    {
        x = 0;
        y++;
        if (y >= v_maxScreenPixelsY)
        {
            y = 0;
        }
    }
    // Need to wrap back to the beginning?
    index++;
    if (index >= v_screenSizeInBytes)
    {
        /******* debug collection **************/
        if (v_debugOn) {
            /* %4d means 4 places of decimal, %2x means 2 places of hex,
```

APPENDIX-continued

```
% means an output */
                fprintf(p_v_ScreenFile,"         doneScreenWorth/wrap
test\n");
                fflush(p_v_ScreenFile);
            }
            /***********DEBUG CODE COLLECT END
****************/
                // Added
                doneCheckingScreenWorth = TRUE;
                index = 0;
                // If we found some changes, send that area. Otherwise,
                // setting index = 0 leads to looking for more changes
                //at the top of the screen.
                if (minx != -1)
                {
                    lastLeftOffIndex = index;
                    break;
                }
            }
        } // end "for" checking all up to v_screenSizeInBytes
/******** "break" statements on "for" above end up here
****************************************/
        // Did we find a rectangle? . . . indicated by minx not being -1
        if (minx != -1)
        {
            byte_length = getScreenRect(minx * v_pixelsPerByte,
                                miny,
                                (maxx + 1)*v_pixelsPerByte-1,
                                maxy);
            p_screenInfo->header.x1 = minx * v_pixelsPerByte;
            p_screenInfo->header.y1 = miny;
            p_screenInfo->header.x2 = (maxx + 1)*v_pixelsPerByte-1;
            p_screenInfo->header.y2 = maxy;
            p_screenInfo->header.skip = 0;// number of horizontal lines that
are skipped between each line
            p_screenInfo->header.format = v_colorFormat;
            p_screenInfo->header.compression = prc_comp_rlCompression;
            // Set pointer to rectangle data.
            p_screenInfo->p_data = v_sendRectangleBuffer;
            /*********** debug collection ****************/
            if (v_debugOn) {
                /* %4d means 4 places of decimal, %2x means 2 places of hex, %
means an output */
                DosGetDateTime(&dt);           // Get Date & Time
                fprintf(p_v_ScreenFile, " %.2d:%.2d:%.2d.%.2d ",
                dt.hours, dt.minutes, dt.seconds, dt.hundredths);
                fprintf(p_v_ScreenFile,"sending
Index => %7dlength => %5d%6d%6d%6d%6d \n",
                    lastLeftOffIndex, byte_length, minx, maxx, miny, maxy);
                fflush(p_v_ScreenFile);
            }
            /*********** DEBUG CODE COLLECT END *************/
            // Send the current screen rectangle.
            // For now ignoring the return from sendScreenData call
            v_p_screenDataMsg->sendScreenData(p_screenInfo,
v_pixelsPerByte);
            } // end if we found a rectangle (i.e. minx != -1)
        } // end while notDoneCheckingScreen's Worth
        } // end while screenThreadActive
        delete p_screenInfo;
        // printf("TheScrnThread is exiting.\n");
    }
    catch ( . . . )
    {
        // No Return
        SYD_systemError(IString("mnt_Screen in catch . . . some uncaught
exception"));
    }
}
/* Function to read video memory */
void
mnt_ScreenTransfer::screenCapture()
{
    NG_TRACE_FUNC();
        unsigned char            *p_dive = NULL;
            unsigned char        *p_current = NULL;
            unsigned int        line = 0;
            unsigned int        i = 0;
            unsigned char         mono_pixels = 0;
```

```
                // remove the pointer from the screen.
                WinShowPointer(HWND_DESKTOP, false);
                    p_dive = (unsigned char *)v_p_diveFrameBuffer;
                p_current = v_currentScreenBuffer;
                if ((v_pixelsPerByte == 8) && (v_platform ==
syt_Programmer::c_486Color9790)) {
                    // BW on Color 9790 Screen capture
                    for(line = 0; line < v_maxScreenPixelsY; line++)
                    {
                        for(i = 0; i < v_maxScreenPixelsX; i++)
                        {
                            mono_pixels < < = 1;
                            if (*p_dive++)
                            {
                                mono_pixels | = 1;
                            }
                            if ((i % 8) == 7)
                            {
                                *p_current++ = mono_pixels;
                            }
                        }
                        p_dive+= mnc_486CUnusedDiveSection;;
                    }
                } // end on if 486C and color off
                    else if (v_pixelsPerByte == 8) {
                        // 386/486EL platform 9790 Screen capture
                        for(line = 0; line < v_maxScreenPixelsY; line++)
                        {
                            for(i = 0; i < v_bytesPerRow; i++)
                            {
                                *p_current++ = *p_dive++;
                            }
                        }
                    } //end if 386/486EL
                    else if (v_pixelsPerByte == 1)
                    {
                        // Color Screen capture
                        /* Copy data from the frame buffer to the memory bitmap. */
                        for(line = 0; line < v_maxScreenPixelsY; line++)
                        {
                            for(i = 0; i < v_maxScreenPixelsX; i++)
                            {
                                *p_current++ = *p_dive++;
                            } // end "for" to copy x
                            p_dive += mnc_486CUnusedDiveSection;;
                        } // end "for" to copy y
                    } // end if 486C and color on
                    else {
                            SYD_systemError(IString("in screen compare and v_pixelsPerByte not 8
nor 1") +
                                    IString(v_pixelsPerByte));
                    }
                    // display the pointer on the screen.
                    WinShowPointer(HWND_DESKTOP, true);
            }
            /* Function to find changed rectangles */
            void
            mnt_ScreenTransfer::screenCompare()
            {
                NG_TRACE_FUNC();
                unsigned int index;
                unsigned char current;
                // printf("The screenCompare is executing.\n");
                index = 0;
                while (index < v_screenSizeInBytes)
                {
                    // compare algorithm is to compare and if different,
                    // copy "current" into "previous" and set a
                    // flag in screenChangedFlagBuffer
                    current = v_currentScreenBuffer[index];
                    if (current != v_previousScreenBuffer[index])
                    {
                        v_previousScreenBuffer[index] = current;
                        v_screenChangedFlagB
uffer[index] = 0xFF;
```

APPENDIX-continued

```
        }
            index++;
        } // end while index < screenSizeInBytes
    // printf("The screenCompare is exiting.\n");
}
```

What is claimed is:

1. A programmer device for use in a medical communications system for communicating in near real time information from between at least two remote sites, one remote site at a patient location having a said programmer device which has a programmer generated display, and another remote site at an expert location having a computing device with a computing device generated display, each location having available substantially similar screen displays, such that information related to an implantable medical device and a patient at said patient location remote site can be reviewed simultaneously on said substantially similar displays at said at least two remote sites facilitated by data communications transferred across a communication line between said at least two remote sites, said programmer device being configurable to perform various operations by executing programs through a microprocessor and memory system and comprising:

a physiologic signal device connection, connected to said programmer device for receiving electrical output representing a patient's physiologic signal waveform and for producing a signal suitable for use by a programmer screen display operating program for generating a display from said electrical output at at least one display area including at least a physiologic waveform signal display area and producing instantaneous changes in said at least one display area, at least one of said changes representative of changes in said waveform display, said programmer operating program, comprising;
      a first video display data buffer for holding a video data representation of information displayed in one of said at least one display areas of said programmer generated display,
      a second video display buffer for holding data representing instantaneous changes in at least one of said areas,
      a display generating program for using a data image of said video data representation in said first video display buffer for producing said programmer generated display,
      an index generating program for reviewing data in said first video display buffer and creating a first index buffer corresponding to said at least one of said display areas, said index generating program indicating in said first index buffer by storing data therein representing which of all locations in said at least one area have changed from a previous review, and for capturing a data representation of said changed locations in a capture buffer and,
      a sending program for packaging data comprising contents of said first index buffer and said capture buffer in appropriately encoded format, and for sending said appropriately formatted index buffer data across said communication line.

2. A programmer device as set forth in claim 1, said display generating program further comprising a two color display generating program for interpreting said physiologic signal waveform as two color display data, and wherein said index generating program has a data compression program for receiving said physiologic waveform index data and coding it such that for each byte, one bit is set to indicate whether a change has occurred in that byte and such that for the entire physiologic waveform index buffer, a compressed physiologic waveform index is prepared.

3. A system as set forth in claim 1 wherein said programmer operating program further comprises;
   a pointer/cursor coordination program having a buffer for holding at least location information for each pointer/cursor to be coordinated, and having a monitoring means for updating any programmer generated display change in pointer/cursor activation and location, said monitoring means updating each said pointer/cursor buffer with any change in location information from a last review, said location information being changeable responsive to pointer/cursor user controls based on a local user changing location status of any pointer/cursor under local control, and wherein said pointer/cursor coordinating program further comprises a buffer for containing information regarding at least location status of each remote pointer that is to be displayed on programmer generated display, and
   programmer operating further comprises;
      a program for receiving new information for each said remote pointer/cursor buffer and operating on such data to produce a display of said remote pointer/cursor in accord with the data in said remote pointer/cursor buffer such that any changes in the location data of a remote pointer/cursor buffer results in a change in location on the display of that remote pointer/cursor on the patient location display screen.

4. A programmer as set forth in claim 3 wherein said pointer cursor operating program further comprises an activation buffer for maintaining activation status for each pointer/cursor capable of activation.

5. A programmer device as set forth in claim 2, wherein said sending program further comprises a pointer data capture program for capturing and then for sending the data in said pointer/cursor buffer to said communication line.

6. A system as set forth in claim 3 further comprising;
   a program for monitoring which of all said pointer/cursors is active such that said active cursor/pointer may initiate a command, and for maintaining a data buffer containing such monitored information.

7. A computing device operating program for coordinating a physiologic waveform display with a programmer generated display as set forth in any of claims 2 and 5, comprising:
   communication means to receive data sent by said programmer device and to produce a physiologic waveform display therefrom.

8. A computing device operating program for displaying an image substantially the same as the display on the programmer generated display having communications means to receive data sent by said programmer device set forth in any of claims 1, 2 and 5 and generating a substantially similar display therefrom.

* * * * *

UNITED STATES PATENT AND TRADEMARK OFFICE
CERTIFICATE OF CORRECTION

PATENT NO.    : 6,325,756 B1                                                Page 1 of 1
DATED         : December 4, 2001
INVENTOR(S)   : James D. Webb et al.

It is certified that error appears in the above-identified patent and that said Letters Patent is hereby corrected as shown below:

Title page,
Item [57], ABSTRACT, delete entire paragraph and replace with:
-- A physiologic signal device is connected across a data communication line, to a programmer that receives electrical output representing a patient's physiologic signal waveform for presentation on one or more programmer screen displays at various remote locations. The programmer display includes a first video display data buffer for holding a video data representation of the information displayed on the programmer and a second video display buffer for holding data representing instantaneous changes in at least one location. A display generating program is implemented to use a data image of the video data image of the video data in the first video display buffer. An index generating program is implemented to review the data in the first video display buffer. Further, a sending program is implemented to package data including the first video display buffer and a capture buffer encoded for transmission across the communication line. --.

Column 24,
Line 32, after "operating" insert -- program --.
Line 55, delete "any of claims 2 and 5," replace with -- claims 1, 2 and 5, --.

Signed and Sealed this

Twenty-fifth Day of February, 2003

JAMES E. ROGAN
*Director of the United States Patent and Trademark Office*